US005763403A

United States Patent [19]

Lian

[11] Patent Number: 5,763,403

[45] Date of Patent: Jun. 9, 1998

[54] SNAKE VENOM LUPUS ANTICOAGULANT PROTEIN

[75] Inventor: Eric Chun-Yet Lian, Coral Gables, Fla.

[73] Assignee: Eric Chun-Tet Lian, Coral Gables, Fla.

[21] Appl. No.: 551,128

[22] Filed: Oct. 31, 1995

[51] Int. Cl.⁶ ................... A61K 38/00; C07K 17/00
[52] U.S. Cl. ................... 514/12; 514/21; 514/822; 530/326; 530/350
[58] Field of Search ................... 514/12, 21, 822; 530/326, 350; 435/13, 39

[56] References Cited

U.S. PATENT DOCUMENTS

| | | | |
|---|---|---|---|
| 4,877,741 | 10/1989 | Babcock et al. | 436/8 |
| 5,453,370 | 9/1995 | Triplett et al. | 435/214 |

OTHER PUBLICATIONS

Fujimura et al, *Biochemistry*, vol. 30, pp. 1957–1964, 1991.
Atoda et al. *J. Biochem*, vol. 118, pp. 965–973, 1995.
Atoda et al. *J. Biol. Chem.*, vol. 266, pp. 14903–14911, 1991.
Usami et al, *Proc. Natl. Acad. Sci, USA*, vol. 90, pp. 928–932, Feb. 1993.
Stocker et al, *Toxicon*, vol. 32, No. 10, pp. 1227–1236, 1994.

Primary Examiner—Cecilia J. Tsang
Assistant Examiner—Abdel A. Mohamed
Attorney, Agent, or Firm—Miller & Christenbury, PC

[57] ABSTRACT

A lupus anticoagulant like protein obtained from *Agkistrodon halys brevicaudus* venom, methods and tests for detecting the presence of lupus anticoagulant in blood and methods of treating antiphospholipid syndrome and thrombotic disorders using the protein are disclosed.

10 Claims, 5 Drawing Sheets

SNAKE VENOM LUPUS ANTICOAGULANT PROTEIN

FIELD OF THE INVENTION

This invention relates to a lupus anticoagulant like protein, particularly a lupus anticoagulant like protein from *Agkistrodon halys brevicaudus* venom, to methods and tests for detecting the presence of lupus anticoagulant and methods of treating antiphospholipid syndrome and thrombosis using the protein.

BACKGROUND OF THE INVENTION

Lupus anticoagulants (LA) are immunoglobulins that interfere with blood coagulation. Lupus anticoagulants are found in the blood of many people. This includes healthy people and those not suffering from lupus erythematosus. They may also be found in people having other immune system disorders such as viral infections including AIDS, tumors such as lymphoma and prostatic carcinoma, rheumatoid arthritis and the like. Such persons having lupus anticoagulants in their blood system may or may not display symptoms. However, they may suffer from disorders such as antiphospholipid syndrome, thrombosis, spontaneous abortion, thrombocytopenia, pulmonary hypertension and the like. Accordingly, there is a great need to accurately determine the presence of lupus anticoagulants in the blood stream and develop methods of treating adverse consequences of the presence of lupus anticoagulants, such as antiphospholipid syndrome, thrombotic disorders such as venous thrombosis, coronary arterial disease such as myocardial infarction (MI), cerebral vascular disease such as stroke, peripheral arterial disease, disseminated intravascular coagulation (DIC) and the like.

There have been a number of attempts to provide viable tests confirming the presence of lupus anticoagulants in the blood stream. However, many such tests have proven to be either not entirely accurate on a consistent basis, excessively complicated to perform on a widespread basis or overly expensive. Many such related attempts are discussed in the following disclosures:

U.S. Pat. No. 4,877,741, TREATMENT OF HUMAN PLASMA WITH BROWN RECLUSE SPIDER TOXIN TO EMULATE A LUPUS ANTICOAGULANT, issued Oct. 31, 1989 to J. L. Babcock et al "The Textarin/Ecarin Ratio: A Confirmatory Test for Lupus Anticoagulants," D. A. Triplett et al, *Thrombosis and Haemostasis, F. K. Schattauer Verlagsgesellschaft mbH (Stuttgart)* 70(6) 925–31 (1993)

"Evaluation of Recently Described Tests for Detection of the Lupus Anticoagulant," R. R. Forastiero et al *Thrombosis and Haemostasis, F. K. Schattauer Verlagsgesellschaft mbH (Stuttgart)* 72(5) 728–33 (1994)

"Comparison of Laboratory Tests Used for Identification of the Lupus Anticoagulant," S. C. L. Lo et al, *American Journal of Hematology* 30:213–220 (1989)

"The Use of the Dilute Russell Viper Venom Time for the Diagnosis of Lupus Anticoagulants," P. Thiagarajan et al, *Blood*, Vol. 68, No. 4 (October), 1986: 869–874

"Guidelines for Testing and Revised Criteria for Lupus Anticoagulants," T. Exner et al, *Thrombosis and Haemostasis, K. Schattauer Verlagsgesellschaft mbH (Stuttgart)* 65(3) 320–32 (1991).

European Pat. EP 0 585 504 A1 published Mar. 9, 1994, D. A. Triplett et al

Not only has it been a longstanding problem in the art to provide a reliable and consistent means for testing for the presence of lupus anticoagulants, it has further been a longstanding problem to provide effective methods of treatment of adverse symptoms exhibited in the presence of lupus anticoagulants, such as antiphospholipid syndrome, thrombosis and the like. These maladies can be highly dangerous to humans and can result in death. It is therefore quite important that treatments overcome such potentially fatal afflictions.

SUMMARY OF THE INVENTION

A lupus anticoagulant like protein (LALP) obtained from *Agkistrodon halys brevicaudus* venom is disclosed. The purified LALP has a molecular weight of 25,500 daltons under non-reducing conditions and 15,000 daltons under reducing conditions. The isoelectric point is pH 5.6. Its N-terminal amino acid sequence is a mixture of two sequences:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS.

The LALP of the invention is devoid of phospholipase A, fibrino(geno)lysis, 5'-nucleotidase, L-amino acid oxidase, phosphodiesterase and thrombin-like activities, which were found in crude venom. In the presence of LALP, prothrombin time (PT), activated partial thromboplastin time (aPTT), and dilute Russell's viper venom time (dRVVT) of human plasma were markedly prolonged and its effects were found to be concentration-dependant but time-independent. The inhibitory effect of LALP on the plasma clotting time was enhanced by decreasing phospholipid concentration in a tissue thromboplastin inhibition (TTI) test. The individual clotting factor activity was not affected by LALP when higher dilutions of LALP-plasma mixture was used for assay.

The invention also includes methods and tests wherein the LALP of the invention may be used as a standardized reference for lupus anticoagulant detection. The method includes conducting a blood test using blood plasma treated with LALP obtained from *Agkistrodon halys brevicaudus* venom and using blood test results as a control for blood having a lupus anticoagulant present. The tests include a freeze-dried lupus anticoagulant control composition including LALP treated blood plasma.

The invention further includes methods of treating antiphospholipid syndrome, DIC and thrombotic disorders wherein a therapeutically effective amount of LALP of the invention is used to treat a patient. Administration of a therapeutically effective amount of LALP in the methods of treating antiphospholipid syndrome and thrombotic disorders causes blockage of binding of human antiphospholipid antibody or factors II, V, VII, VIII, IX and X to effect the treatment.

DETAILED DESCRIPTION OF THE INVENTION

Characteristics of LALP

Figure 5:
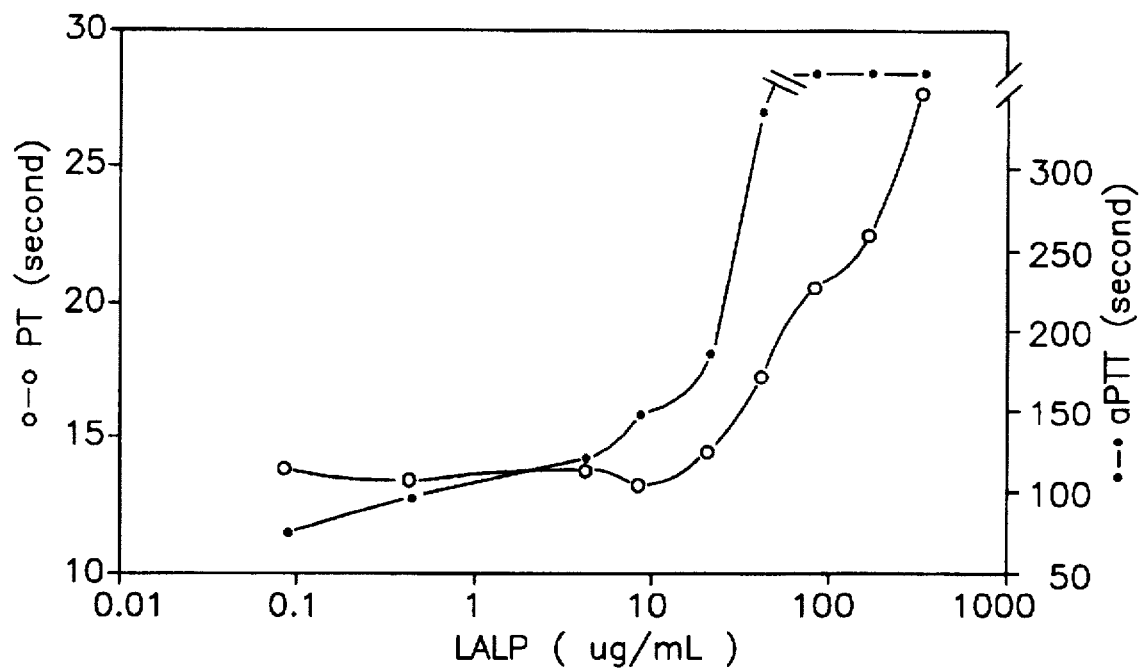
FIG. 5 is a graph of the effect of various concentrations of LALP on PT and aPTT. PT is shown by open circles and aPTT by closed solid circles.
Figure 7:
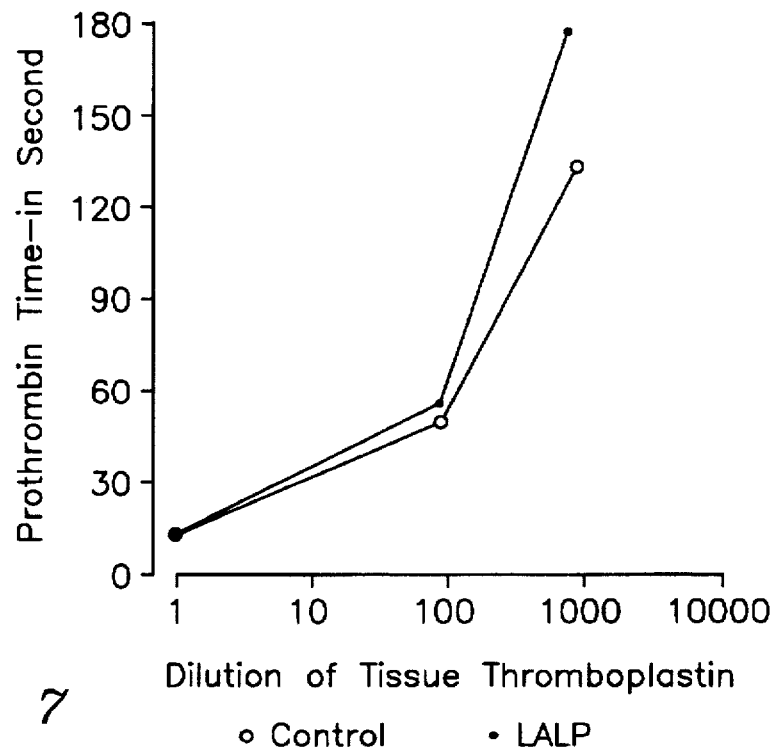
FIG. 7 is a graph showing the effect of LALP on TTI test. Open circles represent the control results without LALP and solid circles represent the results in the presence of 4.4 µg/ml LALP.

The protein purified from *Agkistrodon halys brevicaudus* prolongs prothrombin time (PT) and activated partial thromboplastin time (aPTT) but not thrombin time (TT). This suggests that the protein inhibits coagulation in common pathways or both extrinsic and intrinsic clotting pathways. aPTT and dRVVT were markedly prolonged in the presence of LALP of the invention and its effects were concentration-dependent as shown in FIGS. 5 and 7, but time independent as shown in Table 2. Prolongation of PT and aPTT depends on the concentration of phospholipid used. Each individual clotting activity was not affected by LALP of the invention when proper concentration of phospholipid and dilution of assay mixture were used. Hence, the protein of the invention did not inhibit individual clotting factor activity.

The aPTT reagents contain an activator and a source of phospholipid. The concentration of phosphatidylserine in the aPTT reagent is strongly related to LA sensitivity. The dRVVT test is a sensitivity test for LA which may be readily automated provided the phospholipid and Russell's viper venom are premixed. Therefore, the protein of the invention purified from *Agkistrodon halys brevicaudus* venom behaves like a lupus anticoagulant in humans and is designated as LALP.

The lupus anticoagulant-like protein of the invention consists of two different peptides because the reduced form has only a molecular weight of 15,000. It is devoid of phospholipase A, fibrinogenolysis, 5'-nucleotidase, L-amino acid oxidase, phosphodiesterase and thrombin-like activities, which were found in crude venom. In humans, lupus anticoagulants are immunoglobulins (IgG, IgM or IgA) which interfere with in vitro phospholipid dependent coagulation tests, such as PT, aPTT and dRVVT. These antibodies are not directed at any specific coagulation protein. Instead, they are directed at phospholipid epitopes. LALP of the invention is not immunoglobulin because its molecular weight, isoelectric point and N-terminal amino sequences are different from those of iminunoglobulin. Those sequences are:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS.

Therefore, the two peptides are similar in molecular weight and isoelectric point but not completely identical in amino acid residues on the 4th, 5th, 13th and 15th residues from the N-terminal. These N-terminal 15 amino acid sequences of these two peptides are somewhat similar to that of botrocetin alpha or beta chain and babu coagulation factor IX/X-binding protein. Although the sequences share similarities with botrocetin, the proteins do not contain platelet aggregating activity when added to normal human platelet rich plasma. Therefore, the proteins are quite different from botrocetin. LALP of the invention does not exhibit factor IX/X binding properties because factor IX activity became normal when factor IX was assayed at a higher dilution of LALP-plasma mixture and was affected by the concentration of phospholipid and factor X activity remained normal in the presence of LALP.

The lupus anticoagulant like activity of the LALP of the invention is believed to occur through its binding to phospholipid rather than hydrolysis of phospholipid because the effect of the LALP on phospholipid dependent clotting time is time independent and does not contain phospholipase A.

Detecting LA in Blood

The invention also includes a method of detecting the presence of lupus anticoagulants in blood. First, suitable blood samples are taken and then treated with LALP of the invention. In that regard, pooled normal plasma (PNP) may be obtained as described below, prior to storage at −70° C., for example. PNP is then placed in aliquots in amounts of about 1–10 ml. LALP of the invention in an appropriate buffer may be added to the aliquots to achieve a final concentration of LALP to plasma of about 1–50 µg/ml. The treated plasma may then be incubated at a suitable temperature.

A blank containing buffer only is added to another container of plasma and processed as described above. PT and aPTT tests may be performed to confirm the effects of the protein. It is normally expected that LALP treated plasma exhibits prolonged PT and aPTT times. The buffer treated plasma should obtain normal results.

In the production of a test wherein LALP is used as a control, the treated plasma may be freeze dried by processes well known in the art. Freezing to −70° C. is especially preferred. The result is a freeze dried lupus anticoagulant control composition of LALP treated blood plasma. It is also possible to maintain the LALP treated plasma in wet solution form as desired.

A method of testing for the presence of LA in blood may be performed by first reconstituting the freeze dried treated plasma with water. Of course, this step is omitted when a solution of LALP treated plasma is used. The reconstituted treated plasma is then used to perform a control set of blood tests. Then, blood plasma for which the presence of LA is unknown is obtained and a sample set of blood tests is performed. The results of the sample set of blood tests are compared with the control set wherein the results of the control set are used as a positive control for blood containing lupus anticoagulants.

Treatments Using LALP

The LALP of the invention is useful for treatment of severe antiphospholipid syndrome by blocking the binding of human antiphospholipid antibodies for treatment of thrombosis. It is believed that such treatment prevents clotting factors II, V, VII, VIII, IX and X from binding phospholipids to initiate coagulation.

The method of treating antiphospholipid syndrome includes treatment with a therapeutically effective amount of the LALP of the invention. About 70–700 µg/kg may be administered, preferably intravenously, into the patient.

Similarly, the method of treating thrombotic disorders such as venous thrombosis, coronary arterial disease such as myocardial infarction, cerebral vascular disease such as stroke and peripheral arterial disease includes administering a therapeutically effective amount of LALP to the patient, also preferably intravenously. The preferred concentration for both methods is about 70–700 µg/kg of body weight.

Finally, the invention includes a method of treating DIC which involves administering a therapeutically effective amount of LALP to the patient, preferably intravenously at a concentration of about 70–700 µg/kg of body weight.

Experiments

Materials

The following constitutes most of the materials used in isolating and testing the LALP of the invention. Other materials were used as specifically set forth in the particular tests and assays described below. It should be understood that, in many instances, other materials may be substituted for those described herein without departing from the spirit or scope of the claimed invention.

Venom was obtained from *Agkistrodon halys brevicaudus* snakes located in the Southeast portion of the Peoples Republic of China and in the possession of the Snake Venom Institute of Guangxi Medical University, Guangxi, PRC by usual venom extraction methods well known in the art. CM-Sephadex C-25, DEAE-Sephadex A-50, Sephadex G-200, Sephadex G-75, Ampholine PAGE plates for analytical isoelectric focusing were obtained from Pharmacia LKB Biotechnology, Uppsala, Sweden. Bio-Gel A-0.5M, molecular weight standards for gel filtration and Bio-Rad protein assay kits were obtained from Bio-Rad Laboratories, Richmond, Calif. Tissue thromboplastin (TPL) was obtained from Baxter Diagnostics, Inc., Miami, Fla. Activated partial thromboplastin time (aPTT) reagent, Thrombofax (TFX), was obtained from Ortho Diagnostic Systems Inc., Raritan, N.J. dRVVT kits were obtained from American Diagnostica, Inc., Greenwich, Conn. Factor II, V, VII, VIII, IX, X, XI, and XII deficient plasmas were obtained from George King Bio-Medical Inc., Overland Park, Kan. Bovine thrombin and human thrombin, molecular weight standards for SDS-PAGE and all other chemicals and reagents were purchased from Sigma Chemical Co., St. Louis, Mo. The Fibrometer was obtained from Becton-Dickinson & Company, Cockeysville, Mass. 21030 and the Chrono-log aggregometer was obtained from Chrono-log Corp., Havertown, Pa. 19083.

Figure 1:
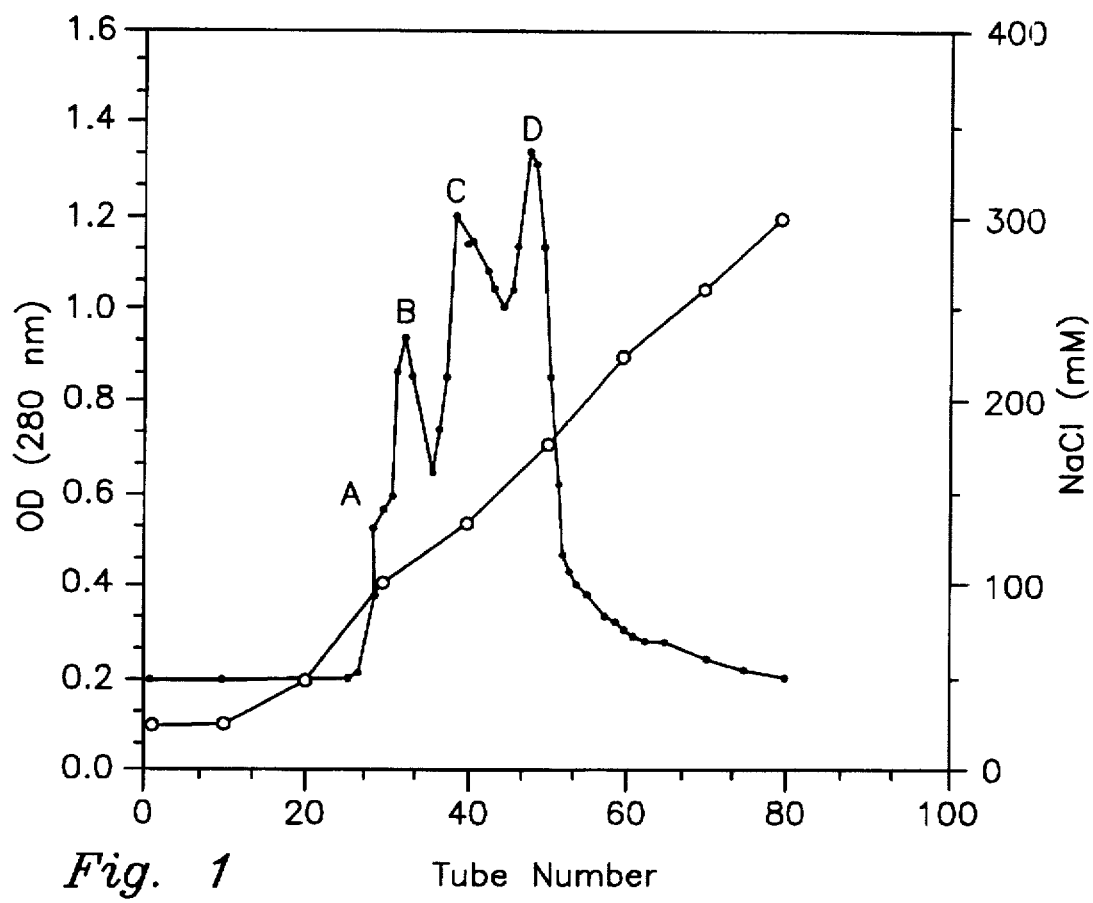
FIG. 1 is a graph of the results of a DEAE-Sephadex A-50 chromatography of the effluent fraction from a CM-Sephadex C-25 column of *Agkistrodon halys brevicaudus* venom showing OD vs Tube number and NaCl (mM) vs Tube number.
Figure 2:
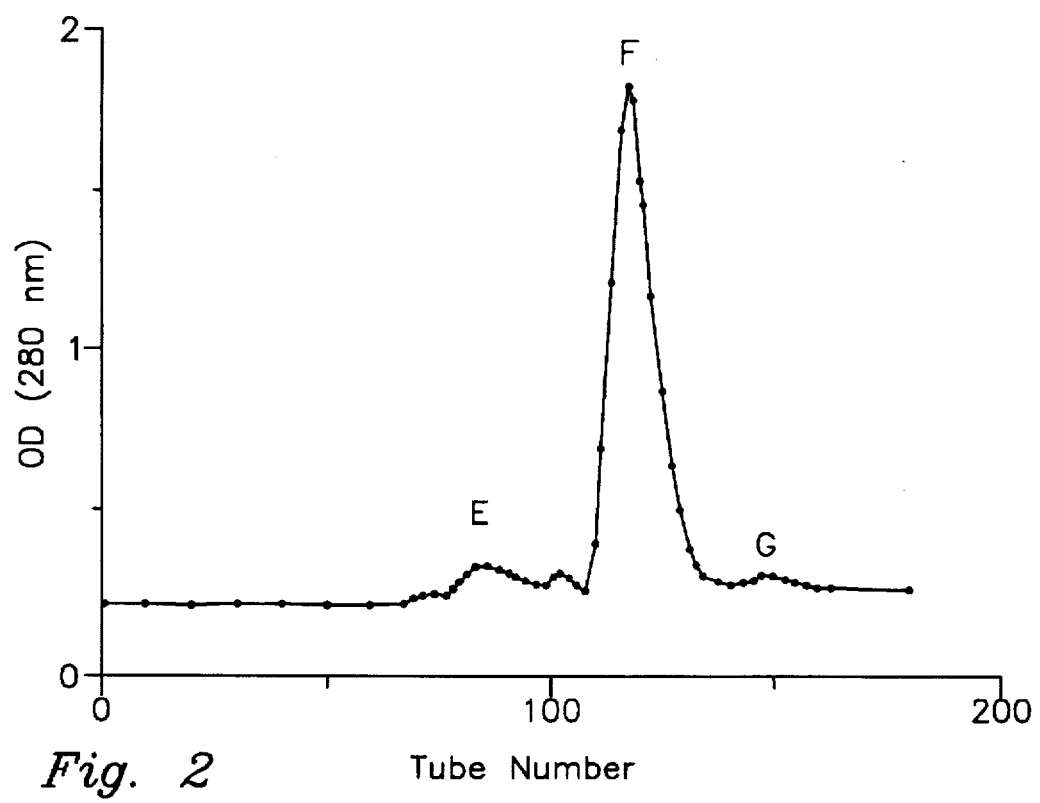
FIG. 2 is a graph showing the results of a Gel filtration of fraction D from FIG. 1 on a Sephadex G-200 column.
Figure 3:
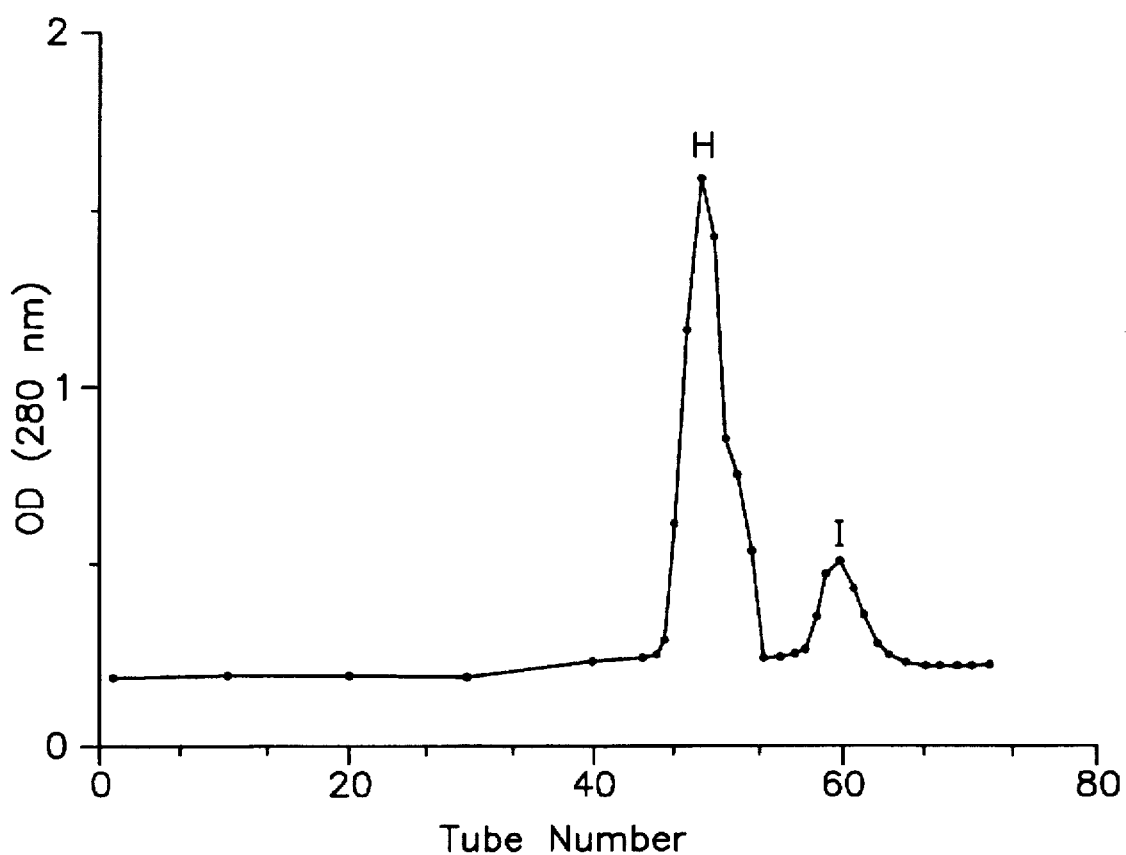
FIG. 3 is a graph showing the results of a chromatography of fraction F from FIG. 2 on a Sephadex G-75 column.

Determination of LALP
Initial Purification of Lupus Anticoagulant Like Protein:

1 gram of lyophilized *Agkistrodon halys brevicaudus* venom was dissolved in 10 ml of 0.05M sodium acetate buffer at pH 5.8 and loaded onto a CM-Sephadex C-25 column (2.6×20 cm) equilibrated with the same buffer. The column was washed with the same acetate buffer at a flow rate of 18 ml/hr. The effluent solution was applied to a DEAE-Sephadex A-50 column (2.6×20 cm) equilibrated with 0.01M Tris-HCl buffer at pH 7.0. After washing, proteins were eluted with a linear gradient of 0 to 0.3M sodium chloride in the same buffer at a constant flow rate of 18 ml/hr. Four protein peak fractions (A, B, C and D) were pooled as shown in FIG. 1. Fraction D caused the prolongation of aPTT and was applied to a superfine Sephadex G-200 column (1.6×100 cm) and eluted with 0.02M Tris-HCl pH 7.4 at a flow rate of 4.2 ml/hr in 1.4 ml fraction. The results are shown in FIG. 2 with peaks E, F and G. Fraction F was loaded onto a superfine Sephadex G-75 column (1.6×100 cm) and eluted with the same buffer at the same flow rate. The fractions exhibiting lupus anticoagulant like activity detected by PT, aPTT and dRVVT tests (as described later) appeared in peak H as shown in Fig. 3.

The fraction H solution had one single protein band on SDS-PAGE under both reducing and nonreducing conditions and two bands by isoelectric focusing gel. The two protein bands in isoelectric focusing gel were cut and electroeluted in the usual well known manner. Only the protein with a pH of 5.6 had lupus anticoagulant-like activity and was designated as lupus anticoagulant-like protein (LALP).

Determination of Isoelectric Point and Molecular Weight of the Protein:

The isoelectric point of the LALP was determined using an electrofocusing ampholine, pH range 4–6.5 in the usual well known manner. The isoelectric point was about pH 5.6.

The molecular weight of the LALP was determined by Bio-Gel A-0.5M (200–400 mesh) filtration chromatography using a 1.6×100 cm column equilibrated with 0.02M Tris-HCl buffer, pH 7.4, and SDS-PAGE using a 10% SDS-PAGE gel in the presence and absence of β-mercaptoethanol. Molecular weight markers were run at the same time for calibration.

Figure 4:
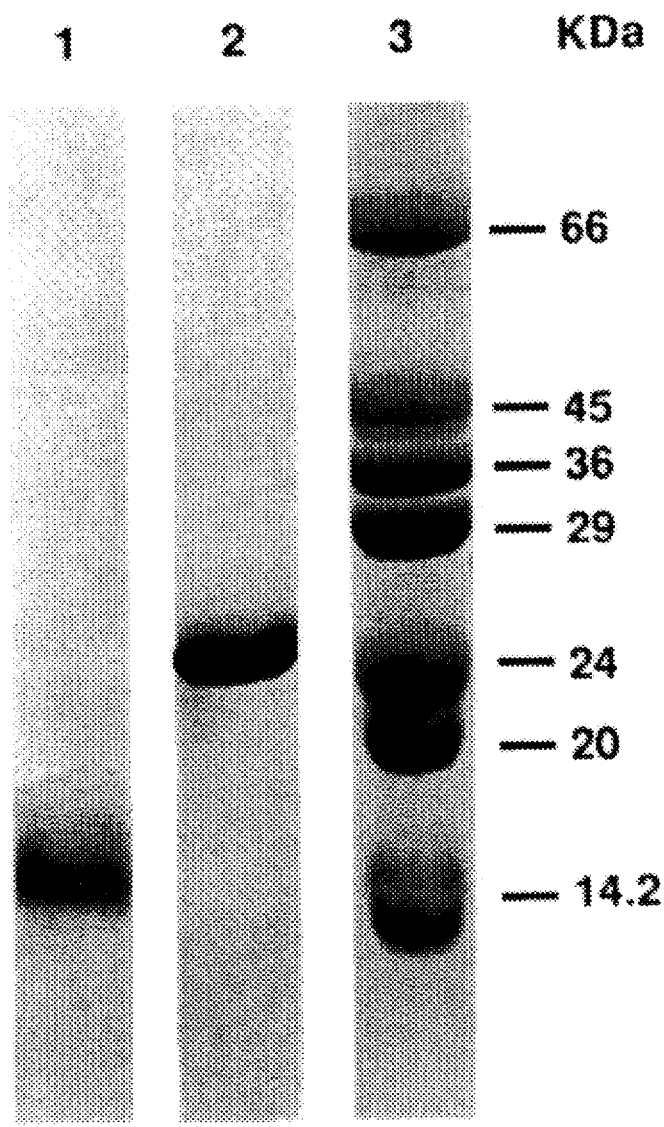
FIG. 4 shows the results of a LALP sodium dodecyl sulfate-polyacrylamide electrophoresis (SDS-PAGE) of purified LALP under reducing (Lane 1) and non-reducing conditions (Lane 2). Molecular weight markers are shown in Lane 3.

SDS-PAGE showed that the β-mercaptoethanol-treated LALP migrated as a single component and had a molecular weight of 15,000 (Lane 1). The non-reduced LALP had a molecular weight of 25,500 as shown in FIG. 4 in Lane 2. The molecular weight of LALP was determined to be about 25,500 by Bio-Gel A-0.5M gel filtration.

Protein Assay:

Protein concentration was determined by the general method of Bradford, "A Rapid and Sensitive Method for the Quantitation of Microgram Quantities of Protein Utilizing the Principle of Protein-Dye Binding," *Analytical Biochemistry* 72, 248–254 (1976) with a Bio-Rad protein assay kit by following the manufacturer's instructions.

The results are shown in Table 1.

TABLE 1

| Protein Standard (mg/ml) | $OD_{595}$ | |
|---|---|---|
| 0.021 | 0.041 | |
| 0.0437 | 0.074 | |
| 0.0875 | 0.152 | |
| 0.175 | 0.241 | |
| 0.35 | 0.413 | |
| 0.7 | 0.828 | |
| 1.4 | 1.620 | |
| Test Fraction | $OD_{595}$ | Protein (mg/ml) |
| 1 | 2.15 | 1.74 |
| 2 | 1.675 | 1.44 |
| 3 | 1.12 | 0.87 |
| 4 | 1.001 | 0.86 |
| 5 | 1.148 | 0.99 |
| 6 | 0.931 | 0.8 |
| 7 | 1.163 | 1.01 |
| 8 | 1.375 | 1.2 |

Test fraction 6 of Table 1, which is the same as peak H in FIG. 3, exhibited lupus anticoagulant-like activity.

N-Terminal Amino Acid Sequencing:

N-terminal amino acid sequencing was performed by ICBR Protein Core Laboratory, University of Florida, Gainsville, Fla. using an automatic Edman degradation method with an Applied Biosystem model 470A gas phase sequencer. The N-terminal amino acid sequencing revealed a mixture of two sequences:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS, indicating that the LALP of the invention contains two non-identical peptides.

Prothrombin Time (PT) and Activated Partial Thromboplastin Time (aPTT):

PT and aPTT were measured by well known methods using TPL and activated PT reagent on a Fibrometer according to the manufacturer's instructions. Prolonged PT and aPTT were observed in the presence of LALP of the invention as compared to the control in the absence of LALP as shown in FIG. 5. LALP had more effect on aPTT than PT at lower concentration (4.4 µg/ml). These effects were time-independent as shown in Table 2.

TABLE 2

Effect of Incubation of LALP and Normal Plasma Mixture on PT and aPTT

| | LALP (µg/mL) | Incubation time (minutes) | | | | | |
|---|---|---|---|---|---|---|---|
| | | 5 | 10 | 15 | 30 | 60 | 120 |
| PT (Seconds) | Exp. 1 | | | | | | |
| | 0 | 12.0 | 11.7 | 11.5 | 11.7 | 11.8 | 11.7 |
| | 4.4 | 11.7 | 11.2 | 11.5 | 11.5 | 11.7 | 11.8 |
| | Exp. 2 | | | | | | |
| | 0 | 15.9 | 15.7 | 15.2 | 14.7 | 14.4 | 15.0 |
| | 177.6 | 24.0 | 22.6 | 23.0 | 23.0 | 25.2 | 24.5 |
| aPTT (Seconds) | Exp. 1 | | | | | | |
| | 0 | 41.9 | 39.2 | 39.0 | 38.7 | 40.7 | 39.0 |
| | 4.4 | 127.3 | 132.4 | 128.9 | 112.7 | 100.5 | 109.0 |

It was determined as a result of these tests that the LALP of the invention had been successfully isolated. However, confirmatory tests were then performed.

Determination of LALP Activity

Subsequent to the isolation of the LALP of the invention, a series of tests were performed, including phospholipase A activity, fibrinogenolytic and fibrinolytic activities, 5'-nucleotidase activity, phosphodiesterase (PDEase) activity, L-amino acid oxidase (L-AAO) activity, platelet aggregation characteristics, prothrombin times (PT), tissue thromboplastin inhibition test (TTI), dilute Russell's viper venom times and clotting factor activities. A separate fractionization of Agkistrodon halys brevicaudus venom was performed to obtain more of fraction F from FIG. 2. The specifics of the fractionization are described below:

500 mg of venom was dissolved in 0.01M Tris-HCl at pH 7.0. The mixture was centrifuged at 1000 rpm at 0° C. for ten minutes. The centrifuged mixture was then unloaded into a DEAE-sephadex A-50 column (1.6×30ml) that was pre-equiliberated with 0.01M Tris-HCl at pH 7.0. Washing was then conducted with the same 0.01M Tris-HCl buffer at pH 7.0. After washing, proteins were eluted with a linear gradient of 0M NaCl in 0.01M Tris-HCl buffer at pH 7.0 to 0.5M NaCl in 0.01M Tris-HCl buffer at pH 7.0 at a flow rate of 18 ml/hr.

Twelve fractions were obtained and pooled as follows:

| | |
|---|---|
| I = 7–11 = 32 ml | VII = 60–67 = 52 ml |
| II = 13–17 = 32 ml | VIII = 70–78 = 60 ml |
| III = 25–32 = 52 ml | IX = 84–91 = 52 ml |
| IV = 37–42 = 39 ml | X = 105–109 = 32 ml |
| V = 45–48 = 26 ml | XI = 113–116 = 25 ml |
| VI = 52–56 = 32 ml | XII = 120–138 = 122 ml |

Figure 6:
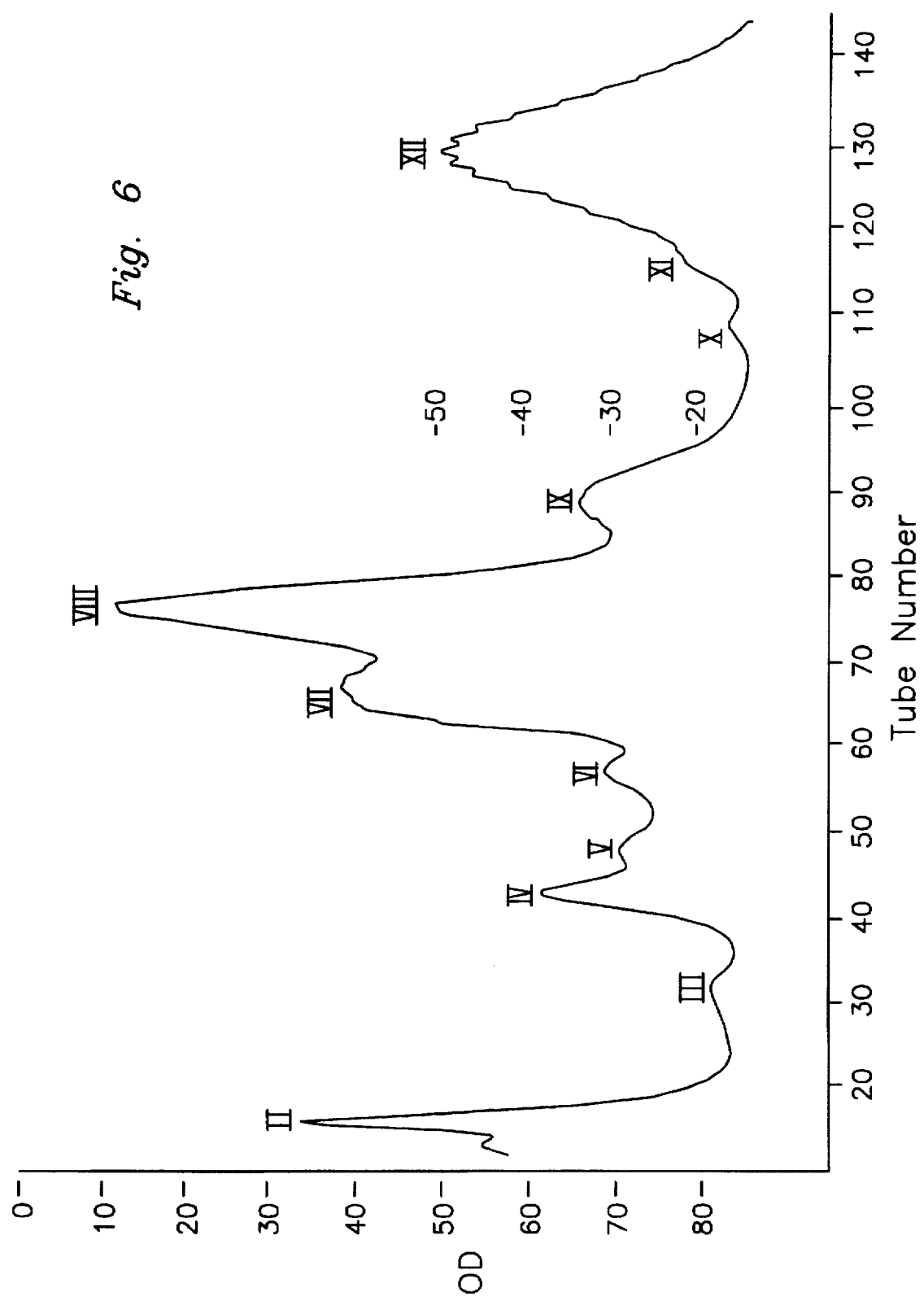
FIG. 6 is a graph of the results of a DEAE-Sephadex A-50 chromotography of *Agkistrodon halys brevicaudus* venom showing OD vs. Tube number.

The results of the fractionization are shown in FIG. 6.

Each of fractions I–XII identified above was then subjected to a series of assays and tests for characterization purposes. Those tests included: L-amino acid oxidase activity, phosphodiesterase activity, fibrinogenolytic activity, fibrinolytic activity thrombin-like enzyme activity, platelet aggregation test and prothrombin time test. The results are shown in Table 3. The remaining tests were taken from the initial venom purification.

L-Amino Acid Oxidase Activity (L-AAO):

L-Amino acid oxidase activity was determined by the method of Wellner et al. "Assay of Amino Acid Oxidase," Academic Press 1971; 17: 593–596 as follows.

A reaction mixture containing 0.4M Tris-HCl buffer, pH 7.8 (80 µmoles), catalase (60 units), and a fraction of eluted L-amino acid oxidase (0.1 ml) in a final volume of 0.7 ml was placed in a 18×150 mm test tube. The reaction was started by addition of 0.1 ml of 0.04M L-phenylalanine and the test tube was immediately placed in a water bath at 37° C. with reciprocal shaking (about 200 cycles/min). After exactly 15 min., the reaction was stopped by adding 0.2 ml 25% trichloroacetic acid. The reaction mixture was transferred to a centrifuge tube and centrifuged. A 0.5 ml aliquot of the supernatant was transferred to a test tube containing 2.5 ml of the borate-arsenate solution and mixed well. The solution was allowed to stand at least 30 min. at 22° C., then the absorbance at 300 nm was measured using a blank in which enzyme was omitted. One unit of L-amino acid oxidase activity was defined as the amount of enzyme required to give an absorbance ($A_{300}$ nm) of 0.03 under the above conditions.

LALP of the invention was determined from fraction XII to be devoid of L-amino acid oxidase activity as shown in Table 3.

Phosphodiesterase Activity (PDEase):

This activity was measured by the well known method of Bjork, "Purification of Phosphodiesterase from Bothrops Atarox Venom, With Special Consideration of the Elimination of Monophophatases," J. Biol. Chem. 1963; 238: 2487–2490 as follows.

A mixture of three solutions contained 1.3 ml of 0.1M Tris-HCl buffer, pH 9.0, 0.3 ml of 5×0.001M $CaCl_2$ and 0.2 ml of enzyme sample or a blank. 1.2 ml of 5×0.1M calcium di-p-nitrophenyl phosphate in Tris buffer was warmed to 37° C. for 5 min and added to the mixture. The reaction mixture was incubated for 5–40 min until a yellow color developed. The reaction was stopped by addition of 3 ml of 0.05M NaOH. The absorbency was determined at 400 in against a blank which contained all components but the enzyme solution. A unit of phosphodiesterase was defined as follows:

$$\text{Activity} = \frac{0.341 \times OD_{400}}{\text{time} \times \text{ml} \times OD_{280}}$$

LALP of the invention was determined from fraction XII to be devoid of phosphodiesterase activity as shown in Table 3.

Platelet Aggregation:

Fresh human blood from normal volunteers was collected for each experiment. The volunteers did not ingest any drugs known to affect platelet aggregation two weeks prior to collection. Platelet-rich plasma (PRP) was prepared from whole blood anticoagulated with 3.8% sodium citrate in a 9:1 ratio by centrifugation at 180 g for 10 min. at 22° C., and the supernatant PRP was harvested. The platelet count in PRP for each assay was adjusted if necessary with platelet-poor plasma (PPP) to about 300,000/μl. All studies were performed in PRP. Platelet aggregation was carried out in a Dual channel aggregometer according to the manufacturer's instructions (Chrono-Log Corp.) at 37° C. by the turbidometric method of Born and Cross, "The Aggregation of Blood Platelets," *J. Pliysiol.* (1963), 168, pp. 178–195. 0.4 ml of PRP was pre-incubated with aggregation inhibitor or 0.02M Tris-HCl buffer, pH 7.4, at 37° C. for 5 min. before addition of the platelet aggregation inducer, L-amino acid oxidase.

In human platelet-rich plasma, LALP neither caused platelet aggregation at 160 μg/ml nor inhibited platelet aggregation induced by collagen (2 μg/ml), ADP (10 μM), or ristocetin (1 mg/ml).

Preparation of Pooled Normal Plasma (PNP)

Blood samples were collected into plastic tubes containing 3.8% sodium citrate in a 9 to 1 ratio. The samples were centrifuged at 2400 g for 20 minutes at 4° C. to obtain PPP. PNP was prepared by pooling PPP from seventeen normal donors who were not on any medication. Afterward, the pooled PPP was centrifuged at 10,000 g for 15 minutes at 4° C., the supernatant was collected, aliquoted and stored at −70° C. until use. The prepared PNP was used in several tests as described below.

Fibrinogenolytic and Fibrinolytic Activities:

These activities were determined by the general method of Ouyang and Teng "Fibrinogenolytic Enzymes of *Trimereusurus Mucrosquamatus* venom," *Biochimica et Biophysica Acta*, 420 (1976) 298–308 as follows.

Fibrinogenolytic Activity (FLE). An equal part of fibrinogen solution (2%) and venom solution (both dissolved in imidazole/saline buffer, pH 7.4) were mixed and incubated at 37° C. for various time intervals. 0.1 ml of the incubation mixture was withdrawn for assay of clottable fibrinogen. In the meantime, 0.2 ml of the incubated solution was pipetted into a test tube, frozen in an acetone/solid $CO_2$ bath and

TABLE 3

| Assay\Fraction | I | II | III | IV | V | VI | VII | VIII | IX | X | XI | XII |
|---|---|---|---|---|---|---|---|---|---|---|---|---|
| L-AAO | − | − | − | − | − | + | ++ | +++ | − | − | − | − |
| PDEase | ++ | ++ | − | − | − | − | − | − | − | − | − | − |
| FLE | − | − | − | − | − | − | − | − | + | − | + | + |
| TLE | − | − | − | − | − | − | − | − | − | − | − | − |
| PTT | >120" | >120" | 102.4" | 92.3" | >120" | >120" | >120" | >120" | >120" | 78.6" | 98" | >120" |

− no activity
+ slight activity
++ some activity
+++ activity

Phospholipase A Activity:

Phospholipase A activity of a sample of fraction F of FIG. 2 was determined using the acidimetric method of Tan and Tan, "Acidimetric Assay for Phospholipase A Using Egg Yolk Suspension as Substrate," *Analytical Biochemistry* 170, 282–288 (1988).

The assay was carried out in a total volume of 15 ml at 25° C. The egg yolk substrate suspension was prepared by mixing 1 part egg yolk (10%), 1 part 18 mM $CaCl_2$, and 1 part 8.1 mM sodium deoxycholate. The pH of the substrate suspension was adjusted to 8.00 with 0.1M sodium hydroxide. The pH of the suspension remained steady for more than 10 min. 100 μl of enzyme sample was added to the substrate suspension to initiate hydrolysis. The suspension was stirred by a magnetic stirrer to ensure good mixing. The pH change between the 5- and 65-second interval was taken as the initial rate of pH change (ΔpH/min). Results are shown in Table 4.

TABLE 4

|  | Fraction f |  | Control |  |
|---|---|---|---|---|
| time | 0 | 5 min. | 0 | 5 min. |
| pH | 7.929 | 7.900 | 7.956 | 7.932 |
| ΔpH |  | 0.006/min. |  | 0.005/min. |

A large ΔpH/min between samples would be indicative of phospholipase A activity since release of fatty acids reduces pH. LALP of the invention was determined to be devoid of phospholipase A activity based on the ΔpH/min similarities between fraction f and the control.

lyophilized. The lyophilized sample was dissolved in 1 ml of the solvent containing 5M urea/2% dodecyl sulfate/2% β-mercaptoethanol in 0.01M sodium phosphate buffer (pH 7.4) and stood overnight. 0.05 ml of this solution was applied to the top of 7.5% acrylamide gel and the same procedure was followed. The fraction XII from the DEAE-Sephadex purification step in Table 3 was shown to contain LALP of the invention and was determined to possess a slight fibrinogenolytic activity due to impurities in the fraction. The highly purified LALP from the final purification procedure was devoid of fibrinogenolytic activity.

Fibrinolytic activity. Four tubes were filled with 0.2 ml of PNP. 0.1 ml of 0.025M $CaCl_2$, was added to each. The mixtures were incubated at 37° C. for 30 min and clots formed. 0.1 ml of buffer was added to two tubes and they were incubated at 37° C. No fribrinolysis was seen at 24 hours. 0.1 ml of LALP was added to the other tubes and incubated at 37° C. No fibrinolysis occurred at 24 hours. In addition, as described later, thrombin time and fibrinogen assay results were not effected by LALP. It was therefore concluded that LALP of the invention is devoid of fibrinolytic activities.

5'-Nucleotidase Activity:

This activity was determined by the well known assay of Dixon and Purdom "Serum 5'-Nucleotidase," *J. Clin. Path.* (1954) 7, 341–343, using adenosine monophosphate as a substrate and as modified below.

0.2 ml of test solution or control (buffer) were incubated with 0.1 ml of 1M glycine-NaOH buffer (pH 9) and 0.1 ml of $MgCl_2$ at 37° C.

At the same time, 0.6 ml of 5 mM 5'-Adenosine monophosphate was incubated at 37° C. for 5 minutes and then added to the above mixture and incubated at 37° C. for 5 to 40 minutes to allow color to develop.

Afterward, the tubes were removed from the incubator and immediately mixed with 1 ml of 10% trichloracetic acid, allowed to stand for a few minutes and centrifuged. One ml of the supernatant was taken out and mixed with 2 ml of substrate solution freshly prepared, which contained 6N $H_2SO_4$, 2.5% ammonium molybdate, 10% vitamin C and $H_2O$ (1:1:1:2 in volumes, respectively). After 20 minutes the colors were read in the spectrophotometer at 800 nm.

The formula used to calculate the activity of 5'-Nucleotidase was:

$$\text{Activity} = \frac{0.31 \times 2 \times OD_{800}}{\text{Time (min)} \times \text{ml} \times OD_{280}}$$

The results were, at $OD_{800}$, control: 0.001 and fraction F from FIG. 2: 0.001. LALP of the invention was thereby determined to be devoid of 5'-nucleotidase activity.

Measurement of clotting factor activities:

To determine which clotting factors were affected by the LALP of the invention in an effort to account for the prolongation of PT and aPTT, all of the clotting factor activities were tested in the presence of LALP. The levels of clotting factors II, V, VII, VIII, IX, X, XI, and XII activities in the presence or absence of LALP were quantitatively determined by well known standard assays commonly used by those of ordinary skill in the art.

In a first experiment, mixtures of 100 μl of PNP as described above and 1 μl of buffer Tris-HCl 0.02M, pH 7.4 (control) or 1 μl of LALP were prepared. The final concentration of LALP was 4.4 μ/ml. Thrombofax was diluted with Tris-HCl 0.02M, pH 7.4 buffer to a 1:20 dilution. Clotting factor assays were then performed for factor VII, factor IX, factor XI and factor XII, with the results shown in Table 5.

TABLE 5

| Factor | Mixture | 1:10 Dilution | | 1:40 Dilution | |
|---|---|---|---|---|---|
| FVIII | PNP + buffer | 132 | >132" | | |
| | | 133 | | | |
| | PNP + LALP | 164 | >163" | 159 | >161" |
| | | 162 | | 163 | |
| | | 20% | | 80% | |
| FIX | PNP + buffer | 68 | >69" | | |
| | | 70 | | 100" | |
| | | | | 52% | |
| | PNP + LALP | 116 | >113" | | |
| | | 110 | | | |
| | | 6.4% | | | |
| FXI | PNP + buffer | 106 | >103" | | |
| | | 101 | | | |
| | PNP + LALP | 120 | >122" | 140 | >140" |
| | | 124 | | 140 | |
| | | 43% | | 90% | |
| FXII | PNP + buffer | 77 | >77" | | |
| | | 77 | | | |
| | PNP + LALP | 82 | >81" | 109 | >110" |
| | | 80 | | 111 | |
| | | 76% | | 80% | |

TABLE 5-continued

| Factor | Mixture | 1:100 Dilution | | 1:1000 Dilution | |
|---|---|---|---|---|---|
| FVIII | PNP + buffer | 180 | >179" | 203" | |
| | | 177 | | | |
| | PNP + LALP | | | | |
| FIX | PNP + buffer | 103 | >104" | 152 | >153" |
| | | 105 | | 153 | |
| | PNP + LALP | | | | |
| FXI | PNP + buffer | 167 | >165" | 204 | >204" |
| | | 163 | | 204 | |
| | PNP + LALP | | | | |
| FXII | PNP + buffer | 128 | >129" | 241 | >239" |
| | | 131 | | 237 | |
| | PNP + LALP | | | | |

In a second experiment, mixtures of 90 μl of PNP as described above and 10 μl of Tris-HCl 0.02M, pH 7.4 buffer (control) or LALP (which contained 4.4 μg) were prepared. The final concentration of LALP was 48.4 μg/ml. Clotting factor assays were then performed for factor II, factor V, factor VII and factor X with the results as shown in Table 6.

TABLE 6

| Factor | Mixture | 1:10 Dilution | | 1:40 Dilution | |
|---|---|---|---|---|---|
| FII | PNP + buffer | 25.5 | >25.3" | | |
| | | 25.0 | | | |
| | PNP + LALP | 25.0 | >24.8" | 38.5 | >38.5" |
| | | 24.5 | | 38.5 | |
| | | 105% | | 124% | |
| FV | PNP + buffer | 33.0 | >33.1" | | |
| | | 33.2 | | | |
| | PNP + LALP | 32.0 | >32.0" | 43.5 | >43.5" |
| | | 32.0 | | 43.5 | |
| | | 112% | | 106% | |
| FVII | PNP + buffer | 33.0 | >33.5" | | |
| | | 34.0 | | | |
| | PNP + LALP | 31.0 | >31.0" | 40.5 | >41.3" |
| | | 31.0 | | 40.0 | |
| | | 140% | | 132% | |
| FX | PNP + buffer | 36.5 | >33.5" | | |
| | | 35.5 | | | |
| | PNP + LALP | 35.0 | >34.8" | 54.0 | >54.0" |
| | | 34.5 | | 54.0 | |
| | | 115% | | 116% | |

TABLE 6-continued

| Factor | Mixture | 1:100 Dilution | | 1:1000 Dilution | |
|---|---|---|---|---|---|
| FII | PNP + buffer | 53.5 | >54.5" | 84.4 | >85.2" |
|  |  | 55.5 |  | 86.0 |  |
|  | PNP + LALP |  |  |  |  |
| FV | PNP + buffer | 53.0 | >53.2 | 62.5 | >62.5 |
|  |  | 53.5 |  | 62.5 |  |
|  | PNP + LALP |  |  |  |  |
| FVII | PNP + buffer | 52.5 | >52.5" | 61.0 | >61.0" |
|  |  | 52.5 |  | 61.0 |  |
|  | PNP + LALP |  |  |  |  |
| FX | PNP + buffer | 76.5 | >77.0" | 138.0 | >138.0" |
|  |  | 77.5 |  | 138.0 |  |
|  | PNP + LALP |  |  |  |  |

The factor VIII, IX, XI and XII tests were then rerun in a third experiment under the conditions below. Mixtures of 100 μl of PNP and 1 μl of buffer Tris-HCl 0.02M, pH 7.4 (control) or LALP (which contained 0.44 μg) were prepared. The final concentration of LALP was 4.4 μg/ml. Thrombofax (TFX) was diluted with Tris-HCl 0.02M, pH 7.4 buffer to a 1:5 dilution.

The clotting factor assays were then performed with the results as shown in Table 7.

TABLE 7

| Factor | Mixture | 1:10 Dilution | | 1:40 Dilution | |
|---|---|---|---|---|---|
| FVIII | PNP + buffer | 90 | >89" |  |  |
|  |  | 89 |  |  |  |
|  | PNP + LALP | 101 | >102" | 115 | >117" |
|  |  | 104 |  | 119 |  |
|  |  | 40% |  | 90% |  |
| FIX | PNP + buffer | 56 | >56" |  |  |
|  |  | 56 |  |  |  |
|  | PNP+ LALP | 75 | >77" | 70 | >70" |
|  |  | 79 |  | 70 |  |
|  |  | 13% |  | 94% |  |
| FXI | PNP + buffer | 74 | >75" |  |  |
|  |  | 75 |  |  |  |
|  | PNP + LALP | 83 | >83" | 99 | >99" |
|  |  | 83 |  | 100 |  |
|  |  | 62% |  | 100% |  |
| FXII | PNP + buffer | 64 | >66" |  |  |
|  |  | 69 |  |  |  |
|  | PNP + LALP | 69 | >69" | 92 | >91" |
|  |  | 69 |  | 91 |  |
|  |  | 76% |  | 78% |  |

TABLE 7-continued

| Factor | Mixture | 1:100 Dilution | | 1:1000 Dilution | |
|---|---|---|---|---|---|
| FVIII | PNP + buffer | 125 | >126" | 169 | >170" |
|  |  | 127 |  | 171 |  |
|  | PNP + LALP |  |  |  |  |
| FIX | PNP + buffer | 79 | >80" | 108 | >110" |
|  |  | 81 |  | 111 |  |
|  | PNP + LALP |  |  |  |  |
| FXI | PNP + buffer | 116 | >117" | 140 | >141" |
|  |  | 118 |  | 142 |  |
|  | PNP + LALP |  |  |  |  |
| FXII | PNP + buffer | 102 | >102" |  | 230" |
|  |  | 101 |  |  |  |
|  | PNP + LALP |  |  |  |  |

LALP of the invention markedly reduced factor VIII, factor IX and factor XI activities when assayed at a lower concentration of TFX (1:20 dilution) compared to a higher concentration of TFX (1:5 dilution). These effects were enhanced in proportion to the increased concentrations of LALP. When TFX was more diluted at 1:20, factor VIII, factor IX and factor XI activities were low, i.e., 20%, 6.4% and 43%, respectively. 1:10 diluted reaction mixture was used for assay and increased to 86%, 52 % and 90%, respectively, when the reaction mixture was assayed at 1:40 dilution. When TFX was less diluted at 1:5 in the assay system, factor VIII, factor IX, factor XI and factor XII activities were 40%, 13%, 62%, and 50%, respectively, when the reaction mixture was assayed at 1:10 dilution and increased to 90%, 94%, 100%, and 120%, respectively, when assayed at 1:40 dilution. Factors II, V, VII and X activities were not affected using the PT method in which tissue thromboplastin was not diluted and the assay reaction mixture was diluted to 1:10, even when these assays were carried out at the concentration of LALP that prolonged PT.

Tissue Thromboplastin Inhibition (TTI) Test:

TTI tests were generally performed according to the well known method of Schleider, "A Clinical Study of the Lupus Anticoagulant," *Blood* 1976; 48: 499–509. Specifically, 90 μl of PNP and 10 μl of buffer were mixed as a normal control. 90 μl of PNP and 10 μl of buffer which contained 0.44 mg of LALP were mixed together. The final concentration of LALP was 4.8 μg of PNP. The mixtures were then incubated at 37° C. for 5 min. Following incubation, 0.1 ml of 25 mM $CaCl_2$ was added, and the clotting time measured. The results are shown in Table 8.

TABLE 8

| | TPL Concentration | | | | | |
|---|---|---|---|---|---|---|
| | Undiluted (1:1) | | 1:100 | | 1:1000 | |
| normal control | 12.4 | >12.5" | 48.4 | >48.7" | 130.6 | >131.7" |
|  | 12.5 |  | 49.0 |  | 132.8 |  |
| PNP + LALP | 11.9 | >11.7" | 54.5 | >54.7" | 176.8 | 176.2" |
|  | 11.5 |  | 54.9 |  | 177.0 |  |

As shown in FIG. 7, which was derived from the results in Table 8, in the TTI test, PT was 54.7 seconds (control 48.7 seconds) at 1:100 dilution of TPL and 176.8 seconds (control 137.7 seconds) at 1:1000 dilution of TPL when LALP was added at 4.4 ug/ml. It was clearly shown that LALP had more effect on TTI at higher dilution of the tissue thromboplastin.

Dilute Russell's Viper Venom Time (dRVVT) Test:

A dRVVT test was performed by using a commercial kit from American Diagnostica, Inc. by following the manufacturer's instructions.

In the dRVVT test, dRVVT was 47.7 seconds and 56.5 seconds (control 41.5 seconds) at 2.2 µg LALP/ml PNP, and 4.4 µg LALP/ml PNP, respectively, suggesting that dRVVT was prolonged in the presence of LALP compared to the control and was dose-dependent.

Thrombin Time (TT) Test:

Thrombin time was determined generally by the method of Machin et al, "Haemostasis Laboratory", *Haematology: Approach to a Haemastatic Problem*, Chanarin I. Ed., Churchill Livingston, N.Y., 1989 pp. 272-280 as follows. 0.1 ml of PNP and 0.1 ml of buffer (Tris-HCl 0.02M, pH 7.4) or LALP were mixed together. The final concentration of LALP was 0.44 mg/ml of PNP. The mixtures were incubated at 37° C. for 1 min. or 5 min. Then, 0.2 ml of thrombin (3.3 units) was added. Clotting times were obtained as shown in Table 9 below.

TABLE 9

|  | Incubation time (min.) | |
|---|---|---|
|  | 1 | 5 |
| buffer control | 18.5" | 18.0 |
| PNP + LALP | 18.5 | 18.5 |
|  | >18.5" | >18.5" |
|  | 18.5 | 18.5 |
|  |  | >18.0" |

Thrombin time was not affected by LALP of the invention.

Fibrinogen Assay

Fibrinogen was measured by the method of Machin et al (identified above) in a clotting assay in the presence and absence of 8.9 µg/ml LALP. In particular, dilutions of 1:5, 1:10, 1:20 and 1:40 of PNP with Owen's buffer were used to establish a normal standard curve. 1:10 and 1:20 dilutions of PNP were prepared, each containing 20 µl of LALP (0.44 mg/ml). The final concentrations of LALP were 0.088 mg/ml of PNP and 0.044 mg/ml of PNP. The mixtures were then incubated for 3 minutes at 37° C. Assays were then conducted in the usual manner with the results shown in Table 10.

TABLE 10

|  | Dilutions | | | |
|---|---|---|---|---|
|  | 1:5 | 1:10 | 1:20 | 1:40 |
| PNP | 5.4 | 9.0 | 20.0 | 41.3 |
|  | >5.5" | >9.0" | >19.7" |  |
|  | 5.5 | 8.9 | 19.5 |  |
| PNP + LALP |  | 11.0 | 20.4 |  |
|  | — | >11.0" | >21.0" | — |
|  |  | 10.9 | 21.0 |  |

Fibrinogen levels were not affected by LALP of the invention.

Although this invention has been described in connection with specific forms thereof, it will be appreciated that a wide array of equivalents may be substituted without departing from the spirit and scope of this invention as described in the appended claims. Also, it should be understood that all possible embodiments of the invention have not been shown in complete detail and that other embodiments are included within the scope of the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 15 amino acid residues
( B ) TYPE: amino acid
( D ) TOPOLOGY: linear ( i i ) MOLECULE TYPE: peptide ( v ) FRAGMENT TYPE: N-terminal fragment ( v i ) ORIGINAL SOURCE:
( A ) ORGANISM: Agkistrodon halys brevicaudus ( x i ) SEQUENCE DESCRIPTION: SEQ ID NO:1:

ASP CYS PRO PRO ASP TRP SER SER TYR GLU GLY HIS CYS GLN GLN
1               5                   1 0                 1 5

( 2 ) INFORMATION FOR SEQ ID NO:2:

( i ) SEQUENCE CHARACTERISTICS:
( A ) LENGTH: 15 amino acid residues
( B ) TYPE: amino acid
( D ) TOPOLOGY: linear (ii) MOLECULE TYPE: peptide (v) FRAGMENT TYPE: N-terminal fragment (vi) ORIGINAL SOURCE:
   (A) ORGANISM: Agkistrodon halys brevicaudus (xi) SEQUENCE DESCRIPTION: SEQ ID NO:2:

```
ASP  CYS  PRO  SER  GLY  TRP  SER  SER  TYR  GLU  GLY  HIS  ARG  GLN  LYS
1                 5                        10                      15
```

What is claimed is:

1. A lupus anticoagulant protein having the sequences:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS.

2. A lupus anticoagulant protein obtainable from *Agkistrodon halys brevicaudus* venom 1) having a molecular weight of about 25,000 Daltons under non-reducing conditions, a molecular weight of about 15,000 daltons under reducing conditions and an isoelectric point of about pH 5.6, 2) being substantially devoid of phospholipase A, fibrino(geno)lytic, 5'-nucleotidase, L-amino acid oxidase, phosphodiesterase and thrombin activities and 3) which prolongs prothrombin time, activated partial thromboplastin time, and dilute Russell's viper venom time.

3. The protein defined in claim 2 wherein said molecular weights are determined by sodium dodecyl sulfate polyacrylamide gel electrophoresis.

4. The protein defined in claim 2 wherein said non-reducing and reducing conditions are caused by the absence or presence of β-mercaptoethanol, respectively.

5. The protein defined in claim 2 wherein said isoelectric point is determined with an electrofocusing ampholine having a pH range of 4–6.5.

6. A composition comprising a protein having lupus anticoagulant activity obtainable from *Agkistrodon halys brevicaudus* venom, said protein having peptides of the N-terminal amino acid sequences:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS.

7. The composition defined in claim 6 wherein said protein has a molecular weight of about 25,500 daltons under non-reducing conditions, a molecular weight of about 15,000 daltons under reducing conditions and an isoelectric point of about pH 5.6.

8. The composition defined in claim 6 wherein said protein is substantially devoid of phospholipase A, fibrino (geno)lytic, 5'-nucleotidase, L-amino acid oxidase, phosphodiesterase and thrombin activities.

9. The composition defined in claim 6 wherein said protein prolongs prothrombin time, activated partial thromboplastin time, and dilute Russell's viper venom time.

10. A lupus anticoagulant protein obtained from *Agkistrodon halys brevicaudus* venom having the sequences:

ASP CYS PRO B J TRP SER SER TYR GLU GLY HIS O GLN W wherein B is selected from the group consisting of PRO and SER, J is selected from the group consisting of ASP and GLY, O is selected from the group consisting of CYS and ARG, and U is selected from the group consisting of GLN and LYS.

* * * * *